United States Patent
Laeng et al.

(10) Patent No.: US 12,396,761 B2
(45) Date of Patent: Aug. 26, 2025

(54) DEVICE, KIT AND METHOD FOR CORRECTION OF SPINAL DEFORMITY

(71) Applicant: DePuy Synthes Products, Inc., Raynham, MA (US)

(72) Inventors: Bruno Laeng, Horriwil/SO (CH); Johann Fierlbeck, Salzburg (AT); Alfred Niederberger, Grenchen (CH); Heiko Koller, Waldeck-Alraft (DE); Laura Villiger, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 18/174,012

(22) Filed: Feb. 24, 2023

(65) Prior Publication Data

US 2023/0190337 A1 Jun. 22, 2023

Related U.S. Application Data

(63) Continuation of application No. 16/539,011, filed on Aug. 13, 2019, now Pat. No. 11,602,378, which is a continuation of application No. 13/937,460, filed on Jul. 9, 2013, now Pat. No. 10,405,893.

(60) Provisional application No. 61/670,903, filed on Jul. 12, 2012.

(51) Int. Cl.
*A61B 17/70* (2006.01)
*A61B 17/86* (2006.01)

(52) U.S. Cl.
CPC ...... *A61B 17/7043* (2013.01); *A61B 17/7001* (2013.01); *A61B 17/7002* (2013.01); *A61B 17/7032* (2013.01); *A61B 17/7034* (2013.01); *A61B 17/7041* (2013.01); *A61B 17/8605* (2013.01)

(58) Field of Classification Search
CPC ................. A61B 17/7032; A61B 17/7037
See application file for complete search history.

(56) References Cited

U.S. PATENT DOCUMENTS

| | | | |
|---|---|---|---|
| 5,643,260 A | 7/1997 | Doherty | |
| 5,702,395 A | * 12/1997 | Hopf | .................. A61B 17/7044 606/265 |
| 5,876,403 A | 3/1999 | Shitoto | |

(Continued)

FOREIGN PATENT DOCUMENTS

| DE | 9314297 U1 | 4/1994 |
|---|---|---|
| DE | 19756646 A1 | 6/1999 |

(Continued)

OTHER PUBLICATIONS

International Patent Application No. PCT/US2013/049640: International Search Report and Written Opinion dated Oct. 16, 2013, 12 pages.

(Continued)

*Primary Examiner* — Tessa M Matthews
(74) *Attorney, Agent, or Firm* — BakerHostetler

(57) ABSTRACT

A device, kit and method for the correction of spinal deformity using an anterior approach. The device comprises a screw-head platform, wherein the screw-head platform comprises a primary recess for receiving a primary rod, and a main vertebral body screw rotatably connected to the screw-head platform.

19 Claims, 6 Drawing Sheets

(56) References Cited

U.S. PATENT DOCUMENTS

| | | | |
|---|---|---|---|
| 5,993,449 A * | 11/1999 | Schlapfer | A61B 17/7044 606/70 |
| 6,136,002 A * | 10/2000 | Shih | A61B 17/7044 606/70 |
| 6,565,569 B1 * | 5/2003 | Assaker | A61B 17/7041 606/264 |
| 6,749,612 B1 | 6/2004 | Conchy et al. | |
| 6,881,215 B2 | 4/2005 | Assaker et al. | |
| 7,008,423 B2 | 3/2006 | Assaker et al. | |
| 7,530,991 B2 | 5/2009 | Nekozuka et al. | |
| 7,909,854 B2 | 3/2011 | Schwab | |
| 7,942,901 B2 | 5/2011 | Rezach | |
| 8,992,579 B1 | 3/2015 | Gustine et al. | |
| 2003/0111088 A1 | 6/2003 | Fox | |
| 2003/0187438 A1 | 10/2003 | Assaker et al. | |
| 2004/0111088 A1 * | 6/2004 | Picetti | A61B 17/7001 606/279 |
| 2006/0084979 A1 | 4/2006 | Jackson | |
| 2007/0093813 A1 | 4/2007 | Callahan et al. | |
| 2007/0093819 A1 | 4/2007 | Albert | |
| 2007/0270817 A1 | 11/2007 | Rezach | |
| 2008/0140130 A1 | 6/2008 | Chan et al. | |
| 2008/0177323 A1 | 7/2008 | Null et al. | |
| 2008/0243186 A1 | 10/2008 | Abdou | |
| 2009/0118768 A1 * | 5/2009 | Sixto, Jr. | B25B 27/064 606/301 |
| 2010/0268279 A1 | 10/2010 | Gabelberger et al. | |
| 2011/0106165 A1 | 5/2011 | Schwab et al. | |
| 2013/0085534 A1 | 4/2013 | Hainard et al. | |

FOREIGN PATENT DOCUMENTS

| | | |
|---|---|---|
| JP | 2001-252283 A | 9/2001 |
| WO | 2014/011580 A1 | 1/2014 |

OTHER PUBLICATIONS

U.S. Appl. No. 16/539,011, filed Aug. 13, 2019.
U.S. Appl. No. 13/937,460, filed Jul. 9, 2013.

* cited by examiner

DEVICE, KIT AND METHOD FOR CORRECTION OF SPINAL DEFORMITY

CROSS REFERENCE TO RELATED APPLICATIONS

This application is a continuation application of U.S. patent application Ser. No. 16/539,011, filed Aug. 13, 2019, which is a continuation application of U.S. patent application Ser. No. 13/937,460, filed Jul. 9, 2013, which claims the benefit of priority to U.S. Provisional Patent Application Ser. No. 61/670,903, filed Jul. 12, 2012, entitled "A DEVICE FOR CORRECTION OF SPINAL DEFORMITY," the teachings of each of which are hereby incorporated by reference as if set forth in their entirety herein.

TECHNICAL FIELD

The present relates to device, kit and methods for correction of spinal deformity. The device is particularly useful in the area of anterior thoracolumbar deformity surgery, including the treatment of scoliosis and deformity related to trauma, infection, tumour and degeneration.

BACKGROUND

The instrumented correction of spinal deformity, and particularly scoliosis, using an anterior approach has been proven to be a successful technical concept. Clinical and scientific work has shown it to be an ideal technique for treating the majority of idiopathic scoliosis types.

In comparison to posterior scoliosis surgery, the use of very early anterior derotation and fusion for selective treatment of thoracic and thoracolumbar curves was shown to save up to two fusion levels compared to the posterior approach. Further, the anterior approach does not disrupt the posterior muscles, it is better at restoring sagittal profile of the spine, it enables real derotation through an anterior column release and direct vertebral manipulation close to the centre of rotation.

As noted above, the use of modern instruments to provide an anterior scoliosis fixation provides significant advantages. A known approach is the use of an instrument with two rods. The use of such a double rod system improves the ease of reconstructing and maintaining a physiologic sagittal spino-pelvic alignment. An exemplary two rod system is described in U.S. Pat. No. 5,702,395. This document describes a spinal osteosynthesis instrumentation for an anterior approach. The instrumentation comprises two rigid rods parallel to each other, and at least two blocks adapted to transversely interconnect the rods, as well as bone anchorage elements for the blocks. The two blocks and the two associated rods make a rectangular frame, which is said to afford all of the required stability for restoring the axial continuity of the vertebral column, avoids correction losses, and facilitates the consolidation of the bone graft.

Recent developments in implant technology have increased the biomechanical stabilisation potential of anterior constructs. Hence, the number of pathologies that can be managed with anterior-only strategies has rapidly increased.

However, with both anterior-only scoliosis correction and reconstruction of the anterior column in other deformities, the amount of corrective force applied to the instrumentation is limited by the interface strength and pull out resistance of the screws anchoring the instrument to the vertebral body. Hence, further development of implants and screws used for anterior spinal surgery has the potential to increase construct stability, broaden the indications for which anterior column surgery is suitable and push the limits of current techniques and corrections that are currently achieved.

SUMMARY

It is an object of the present disclosure to improve the angular stability of a device for correction of spinal deformity using an anterior approach.

It has been found that connecting a main vertebral body screw to a screw-head platform so that the main vertebral body screw cannot move in its axial direction relative to the screw-head platform advantageously ensures that the main vertebral body screw has a stable angular relationship relative to the screw-head platform. This angular stability of the main vertebral body screw relative to the screw-head platform ensures that the screw direction is at a constant angle relative to the screw-head platform. Therefore, there is limited possibility for potentially unpredictable angular changes between the main vertebral body screw and the screw-head platform during or after implantation. Such unpredictable changes may be particularly problematic after implantation as it will adjust how the spine is being corrected. Further, the connection of the main vertebral body screw to the screw-head platform reduces the number of parts that need to be assembled during surgery and thus decreases the complexity of the implantation procedure. It also reduces the possibility of losing either of the main vertebral body screw or screw-head platform during the operation as they are connected to each other.

It has also been found that providing a screw-head platform that aligns a main vertebral body screw in the same plane as an anchor screw reduces the required size of the screw-head platform, in particular, in the cranial-caudal direction. This is therefore a more efficient use of space inside the vertebral body, in particular, thoracic and cervical vertebral bodies, to which the device will be affixed, where space is limited. Further, the triangulation of the screws increases the resistance against pull out and cyclic loads. Such an arrangement can also be used to ensure that the anchor screw, which is attached after the main vertebral body screw, does not extend beyond the main vertebral body screw and potentially damage the spinal cord. This can be achieved by making sure that the path of the anchor screw converges to a point along the main vertebral body screw and so would contact the main vertebral body screw before penetrating beyond it.

According to the present disclosure, there is provided a device for correction of spinal deformity using an anterior approach comprising a screw-head platform, wherein the screw-head platform comprises at least one or a primary recess for receiving a primary rod; and a main vertebral body screw rotatably connected to the screw-head platform.

The present disclosure also provides a device for correction of spinal deformity using an anterior approach comprising a screw-head platform, wherein the screw-head platform comprises at least one recess, for instance a primary recess, for receiving a primary rod. The screw-head platform comprises a main bore for receiving a main vertebral body screw and an anchor bore for receiving an anchor screw. The main bore and the anchor bore are positioned so as to align the anchor screw at an oblique angle relative to the main vertebral body screw in a common plane with the main vertebral body screw.

As stated above, the devices, kits, and methods described herein are suitable for use with any anterior thoracolumbar deformity surgery. These include the treatment of scoliosis and deformity related to trauma, infection, tumor and degeneration.

The screw-head platform is the component through which the one or more corrective rods (primary rod and, possibly, secondary rod) are attached to the patient's spine in order to correct the spinal deformity. The screw-head platform is attached to the vertebral body of the patient by the main vertebral body screw. In alternative embodiment, the device includes an anchor screw. In general, it is desirable to have a screw-head platform that is as small as possible while still possessing its full function and mechanical stability. In particular, a low profile of the screw-head platform above the vertebral surface to which it is attached is very important due to the limited space around the patient's spine. These space constraints are particularly acute in the case of correcting spinal deformities in younger patients. The screw-head platform can a low profile and a low volume.

The underside of the platform is shaped in a complementary manner to the surface of the vertebra to which it is to be attached. In this way, the height of the screw-head platform off of the vertebral surface can be minimized. The underside of the screw-head platform can be concave, in particular, in a longitudinal direction, or cranial-caudal direction when implanted, to complement the anatomical shape of the surface of the vertebral body. The underside of the screw-head platform refers to the screw-head platform surface that faces the vertebra when the device is in use. The underside can be the surface through which the main vertebral bod and anchor screws protrude to affix the screw-head platform to the vertebra.

The screw-head platform comprises at least one, for instance a primary recess, that is configured to receive a primary rod. The primary recess can define U-shaped channel running through the screw-head platform with an open top. The open U-shape of the channel allows the primary rod to be easily inserted into the recess. The recess can have a width that corresponds approximately to the diameter of the primary rod. The width of the recess can allow the rod to be inserted into the recess while reducing the lateral (i.e. along a lateral direction that is perpendicular to the length direction of the rod) movement of the rod within the recess. This decreased potential for movement increases the overall mechanical stability of the deformity correction system.

Securement of the primary rod can be further supported by the primary recess having a complementary shape to that of the primary rod. This can increase the size of the contact area between the screw-head platform and the primary rod and so further reduces the potential movement, particularly lateral movement, of the primary rod when it is fully seated in the primary recess. The primary rod may also be held or contacted within the recess by a component that is shaped in a complementary manner to the primary rod so as to restrict the primary rod's movement, in particular its lateral movement. Such an additional contacting component may be part of the securing means described below. The configuration of the primary recess apply to the secondary recess, described below, if present.

The screw-head platform is generally elongate in shape along the lateral direction. The primary recess for receiving the primary rod generally runs through the screw-head platform in a direction that is perpendicular to the screw-head platform's elongate direction or lateral direction. The elongate shape of the screw-head platform can accommodate the main vertebral body screw and an anchor screw.

The main bore in the screw-head platform is sized to receive the main vertebral body screw. The main bore may be shaped to have a complementary surface to the underside of the head of the main vertebral body screw so that the main vertebral body screw is supported in its axial direction when the main vertebral body screw is fully seated within the main bore.

The main bore is positioned at the base of the primary recess so that the main bore, and the head of the main vertebral body screw when it is in the main bore, may be accessed via the recess prior to the insertion of the primary rod into the primary recess. After insertion of the primary rod in the primary recess, the primary rod obstructs access to the main bore or the head of the main screw in the primary recess. This arrangement keeps the size of the screw-head platform small as independent access to the main bore, distinct from that of the primary recess, does not have to be accommodated for in the screw-head platform.

As noted above, the main vertebral body screw may be rotatably connected to the screw-head platform. This has the effect of restricting the axial movement of the main vertebral body screw relative to the screw-head platform, while still allowing relative rotational movement. In other words, the rotatable connection ensures that the vertebral body screw cannot move in the axial direction of the main vertebral body screw, i.e. the movement of the main vertebral body screw in its axial direction is substantially prevented. The axial direction of the main vertebral body screw runs along the length of the screw and is the direction in which the screw penetrates the body to which it is being affixed. The inability of the main vertebral body screw to move in its axial direction has the results highlighted above. Namely, the angular relationship between the main vertebral body screw and the screw-head platform will remain constant as restraining the main vertebral body screw from moving in the main vertebral body screw's axial direction eliminates any differential axial movement across the diameter of the main vertebral body screw. Such differential axial movement would cause the alignment of the main vertebral body screw with the screw-head platform to change. Further stability is achieved by the axial movement restriction by ensuring that the main vertebral body screw is retained properly seated within the main bore of the screw-head platform. This means that the head of the main vertebral body screw can be fully supported by the complementary surface of the main bore.

The main vertebral body screw axial movement restriction removes the angular relationship between the main vertebral body screw and the screw-head platform as a concern during surgery and so the use of such a device increases the speed and reliability of performing a spinal deformity correction. Further, the axial retention of the main vertebral body screw also minimises the possibility that the main vertebral body screw will move relative to the screw-head platform during subsequent manipulation of the vertebra to which it is connected. This again increases the reliability of the device and the predictability of its subsequent behaviour after being affixed to the patient's vertebra. Also, connecting component parts of the device together before surgery reduces the chance of losing either component during the operation.

The connection between the main vertebral body screw and the screw-head platform is such that it restricts relative axial movement but allows relative rotational movement, i.e. it fixes the axial movement of the main vertebral body screw relative to the screw-head platform but it does not fix the rotation movement of the main vertebral body screw relative to the screw-head platform. This allows the main vertebral body screw to be screwed into the vertebra body of the patient while maintaining the screw-head platform in the desired rotational orientation. The screw-head platform may comprise a retention component to perform the function of connecting the screw-head platform to the main vertebral body screw, restricting relative axial movement while allowing relative rotational movement. Such a retention component may be an integral part of the screw-head platform or it may be a separate component that is attached to the screw-head platform.

In order to provide the connection between the main vertebral body screw and the screw-head platform, the main vertebral body screw may have an annular indentation. The screw-head platform may then have a retention component that can interact with this annular indentation in order to constrain the axial movement of the main vertebral body screw. In particular, the retention component of the screw-head platform may protrude into the annular indentation provided on the main vertebral body screw and so constrain its axial movement. It will be appreciated that a protrusion that closely fits the annular indentation would minimize the play between the protrusion in the annular indentation.

The retention component may comprise an annular protrusion so that the retention component protrudes into the annular indentation of the main vertebral body screw all the way around the screw. However, the retention component may only protrude into part of the annular indentation. For example, the retention component may protrude into the annular indentation so that it protrudes into between 180° to 360° of the annular indentation. An example of such a retention component would be a C-clip. Alternatively, the retention component may only protrude into less than 180° of the annular indentation of the main vertebral body screw, alternatively less than 90° of the annular indentation of the main vertebral body screw. The retention component may comprise a single continuous protrusion that is received in the annular indentation of the main vertebral body screw. Alternatively, the retention component may comprise a plurality of discrete protrusions that protrude into the annular indentation. A higher amount of the retention component protruding into the annular indentation of the main vertebral body screw will improve the stability of the axial constraint. Decreasing the proportion of the annular indentation that contains a protrusion of the retention component will lower the frictional resistance provided by the retention component to the main vertebral body screw's rotational movement.

Other retention components are of course possible as the skilled person would understand. For example, the retention component could comprise a pin arranged to engage with the annular indentation. In one example, a pin or a plurality of pins may be passed through the screw-head platform into the annular indentation, the pins then being fixed in position. In another example, the pin or pins may be biased to protrude from the screw-head platform, the pin, or pins, being displaceable against this bias. This allows the main vertebral body screw to be inserted into the main bore of the screw-head platform by displacing the pin, or pins, out of their protruding arrangement. The pin, or pins, will then resiliently snap back to protrude into the annular indentation to restrict further axial movement of the main vertebral body screw.

Where the retention component comprises a plurality of discrete protrusions that protrude into the annular indentation, the plurality of discrete protrusions can be arranged symmetrically when protruding into the annular indentation of the main vertebral body screw. This reduces the presence of less stable directions of the main vertebral body screw. Further, the plurality of discrete protrusions number at least three to ensure a certain level of stability is provided by the retention component.

As indicated above, the main vertebral body screw is able to rotate relative to the screw-head platform in order to allow it to be screwed into the vertebra of the patient. The above described retention components are such as to allow this relative rotational movement while inhibiting the axial movement of the main vertebral body screw.

The screw-head platform may further comprise an anchor bore. The anchor bore is sized so as to receive an anchor screw. The anchor bore may be such that when it receives the anchor screw, it aligns the anchor screw at an oblique angle relative to the main vertebral body screw. In other words, the anchor bore is such so as to align the anchor screw so that the line along the length of the anchor screw (the anchor screw's axial direction) is angled with respect to the line running along the length of the main vertebral body screw (the main vertebral body screw's axial direction) so that the anchor screw's axial direction is neither parallel nor at a right angle to the main vertebral body screw's axial direction. The presence of an anchor screw in addition to the main vertebral body screw improves the pull out resistance of the device. This is of great benefit because conditions such as scoliosis are often associated with poor bone quality of the vertebra.

The anchor screw may have angular stability relative to the screw-head platform. This angular stability increases the overall reliability and stability of the device. Such angular stability can be provided by the anchor bore comprising a thread that can interact with a thread on the head of the anchor screw as the anchor screw is secured into the anchor bore.

The anchor screw is not connected to the screw-head platform in the manner described above with respect the main vertebral body screw above. While anchor screw is configured so that axial movement of the anchor screw is possible. In this way, the anchor screw will not necessarily be present when securing the main vertebral body screw into the patient's vertebra, which could result in the anchor screw interfering with this operation. This thus avoids an increase in the complexity of the securing operation.

The anchor bore may also be positioned so as to align the anchor screw in a common plane with the main vertebral body screw. Hence, the anchor screw's axial direction and the main vertebra body screw's axial direction will both fully lie in a same plane. Such an arrangement allows the screw-head platform to remain small resulting in efficient use of space within the patient's body and within the vertebral body to which the screw-head platform is attached. Such an arrangement of the anchor screw and the main vertebral body screw is also beneficial in terms of biomechanical concerns, increasing the stability of the device.

The angle between the anchor screw's axial direction and the main vertebral body screw's axial direction when both screws are properly seated in the screw-head platform is based on the anatomical situation. In particular, it has been found that the range of angles of 15° to 30° is particularly acceptable. In an exemplary embodiment, the angle $\theta$ is approximately 20° degrees between the anchor screw's axial direction and the main vertebral body screw's axial direction. The angle between the anchor screw's axial direction and the main vertebral body screw's axial direction is the acute angle formed between the axial direction of the main vertebral body screw and the axial direction of the anchor screw. The axial directions of the screws run along the length of the screws and in the direction in which the screw will travel when being screwed into a body.

The common plane between the anchor screw and the main vertebral body screw is perpendicular to the direction in which the primary rod runs when received in the primary recess of the screw-head platform, i.e. perpendicular to the length of the primary rod when it is received in the primary recess. Again, this ensures that the screw-head platform can maintain a small dimension in the direction parallel to the primary rod's length when received in the primary recess. The reduction of the dimensions of the screw-head platform has the advantages highlighted above.

The height of the screw-head platform is approximately 15 mm or less, for example, the height of the screw-head platform may be 12 mm or may be 10 mm. The height of the screw-head platform is the distance measured perpendicular from the screw-head platform surface that faces the vertebra body in use to the surface opposite. In other words, the screw-head platform height is a measure of how far the screw-head platform rises above the underside of the screw-head platform. Ensuring that the screw-head platform's height is as low as possible improves the space efficiency of the device and reduces the interference caused by the screw-head platform in situ.

The screw-head platform is of a generally rectangular shape. Specifically, the underside of the screw-head platform, which contacts the vertebra body, is of a rectangular shape to accommodate the screws and the rods. Both the length and the width of the rectangular screw-head platform are 30 mm or less, in particular, the length and width of the rectangular screw-head platform are 25 mm or less. Again, this keeps the screw-head platform compact so that it does not interfere when in situ and efficiently uses the space available in the patient's body.

As noted above, the screw-head platform is shaped to receive a primary rod. The screw-head platform may also comprise a secondary recess, similar to the primary recess, for receiving a secondary rod. This secondary recess runs parallel to the primary recess in order to receive a secondary rod that is parallel to a primary rod. The secondary recess is sized in accordance with the size of the secondary rod that is to be used. The use of two rods results in a supportive rectangular frame that helps support the readjusted spine.

The device of the present disclosure may comprise a means for securing the primary rod to the screw-head platform. The device may also include a means for securing the secondary rod to the screw-head platform.

The means for securing the primary rod or the means for securing the secondary rod may comprise a top loading screw. A top loading screw seals the recess into which the rod is placed. In other words, the rod is placed in the open recess and the top loading screw secures the rod by blocking the top of the recess so that an enclosed channel is formed in which the rod is held. The rod is inhibited from rotating or sliding within the channel by the top loading screw applying a sufficient pressure to the rod. A top loading screw as a securing means can be used for just one of the primary recess or secondary recess. Alternatively, a top loading screw can be used as a securing means with both the primary recess and the secondary recess.

The use of a top loading screw is advantageous as it provides an easier way of securing a rod. This is due to the relatively wide tolerance in the position of the rod prior to the commencement of securing using the top loading screw. Screwing of the top loading screw then gradually confines the rod to its secure position within the recess. Top loading screws also reduce the length and/or width requirements of the screw-head platform as they secure the rod by aligning with a central axis of the rod. Whereas, the use of side loading screws, considered below, requires additional room within the screw-head platform in which to accommodate a screw besides the received rod.

An alternative means for securing the primary rod or for securing the secondary rod is a side loading screw. Side loading screws are positioned adjacent the recess and possess a conical head. The conical head overhangs the recess. Therefore, loosening the side loading screw increases the gap into which the rod can be placed. After placing of the rod in the recess beneath the conical head of the side loading screw, the screw is tightened so that the rod is held in position by the conical head. Such side loading screws occupy less height for a given mechanical stability when compared to top loading screws. However, it can be difficult to introduce a rod into a recess with a side loading screw and subsequently secure the rod.

Although any combination of top loading and side loading screws can be used with the device of the present disclosure, a top loading screw can be used with the primary recess as previous work has shown that using the top loading screw is easier to attach to the screw-head platform. The secondary rod can be secured by either a side loading screw or a top loading screw, which will result in the relevant advantages described above. It is possible to use a side loading screw for securing both the primary rod and the secondary rod. However, the use of two side loading screws would make the platform longer, which could be problematic in certain spinal deformity surgery such as with adolescent vertebrae, where space within the patient is restricted. In particular, it is possible have a top loading screw for securing the primary rod and a top loading screw for securing the secondary rod. Alternatively, it is possible to have a top loading screw for securing the primary rod and a side loading screw for securing the secondary rod.

The device may comprise a primary rod for securing in the primary recess. The device may also include a secondary rod for securing in the secondary recess. The primary rod can have a diameter of 5.0 mm or greater. Further, the primary rod can have a diameter of 5.5 mm or less. In an exemplary embodiment, the primary rod is about 5.5 mm in diameter. The secondary rod has a diameter of 3.5 mm or greater. Further, the diameter of the secondary rod is 4.0 mm or less.

The device may also comprise an anchor screw. The anchor screw is received in the anchor bore as described above.

All of the parts of the device may be made from any suitable biocompatible material. Exemplary materials are metallic materials. Suitable metallic materials include cobalt-chrome alloys, titanium, and stainless steel.

The device comprises a plurality of screw-head platforms each of the screw-head platforms receives and secures the primary rod, and possibly the secondary rod, to various parts of the spine. The combination of the platforms and the rod(s) as described herein allows the spine to be manipulated and supported for correcting spinal deformities.

Each of the plurality of screw-head platforms can have the features described above. In particular, each of the screw-head platforms may comprise the same features or different features to each of the other screw-head platforms. In particular, each of the plurality of screw-head platforms will have a main vertebral body screw associated with them so that each platform can be secured to the patient's spine, offering support and allowing manipulation.

In general, when in use the screw-head platforms are secured to the lateral circumference of the vertebra body and the underside of the screw-head platform rests on the surface of the vertebra. The screw-head platform is shaped with a curvature that enables the underside of the screw-head platform to fit best to the vertebra body. Such curvature will minimise the gap between the underside of the screw-head platform and the body of the vertebra. This also reduces the profile of the screw-head platform off of the vertebra body.

The present disclosure also provides a kit for correction of spinal deformity using an anterior approach. The kit includes a screw-head platform, wherein the screw-head platform comprises a primary recess for receiving a primary rod and a main bore for receiving a main vertebral body screw; a main vertebral body screw; and a retention component for connecting the screw-head platform to the main vertebral body screw so that the main vertebral body screw cannot move relative to the screw-head platform in the axial direction of the main vertebral body screw.

Such a kit of parts may comprise additional features or parts as recited above. The kit of parts for assembling a device of the present disclosure enables the device to be in a disassembled state for ease of transport and to be then subsequently assembled before or during the operation in which it will be used.

The retention component referred to above may be integral to the screw-head platform or it may be a separate component which is subsequently secured to the screw-head platform so as to perform the task of retaining the main vertebral body screw relative to the screw-head platform.

The present disclosure also provides a method of correcting a spinal deformity using an anterior approach with the devices of the present disclosure, comprising the steps of affixing a screw-head platform to a patient's spine by screwing the main vertebral body screw into the lateral surface of the vertebral body; inserting the primary rod into the screw-head platform's primary recess; and securing the primary rod within the primary recess.

The use of a device of the present disclosure with the above described method improves the ease with which the surgery can be performed as well as the reliability of the procedure. This is due to the various features described above. For example, connecting the main vertebral body screw to the screw-head platform decreases the likelihood that the screw will be lost during the operation as well as reducing the chance that the angle between the main vertebral body screw and the screw-head platform will change during or after the operation. Further, the presence of an anchor screw that is aligned by the screw-head platform in a common plane with the main vertebral body screw reduces the required size of the screw-head platform and so decreases the space required when implanting the screw-head platform in the patient's body.

In addition to the screw-head platform being affixed by the main vertebral body screw, an anchor screw can also be screwed into the lateral surface of the vertebral body, through the screw-head platform, so as to further secure the screw-head platform in position. The anchor screw can be screwed into the vertebral body after the main vertebral body screw has been screwed into position.

After inserting the primary rod into the primary recess, the primary rod may be secured within the primary recess by applying and screwing a top loading screw so as to contain the primary rod between the top loading screw and the screw-head platform.

The method may comprise affixing a plurality of screw-head platforms to the patient's spine and then inserting a primary rod into each of the screw-head platforms and securing the primary rod in each of these screw-head platforms. The insertion of the primary rod into each of the screw-head platforms may be associated with a level of spinal manipulation. The securing of the primary rod then holds this manipulation in place. In this way, the patient's spine can be manipulated and supported to correct the spinal deformity.

The method may also comprise inserting a secondary rod into a secondary recess in the screw-head platform. This is then followed by the securing of the secondary rod within the secondary recess, either by applying and screwing a top loading screw or by screwing a side loading screw so as to contain the secondary rod between the screw-head platform and the screw. The securing of the secondary rod occurs after the securing of the primary rod, the primary rod being typically designed to withstand greater forces than the secondary rod. When there are a plurality of screw-head platforms present, the primary rod can be secured in all of the plurality of screw-head platforms before the secondary rod is secured in any of them. Alternatively, the primary rod and then the secondary rod can be secured into each screw-head platform, primary rod first, before commencing the insertion and securing of the primary rod and secondary rod in the next screw-head platform.

The device of the present disclosure can be implanted by performing a thoracotomy, a thoracolumbophrenotomy, or by using an endoscopic approach. The vertebral column is exposed and the lateral surface of the vertebral body is dissected to remove the soft tissue. A small awl is used to form a pilot hole for the main vertebral body screw. This pilot hole is usually close to the plane of the rib heads, parallel to the end plates in the axial plane, albeit perpendicular to the lateral vertebral body surface slightly directing anteriorly off the spinal canal. The length of the screw and screw tract preparation can be assessed based on previous MRI and/or CT based measurements of vertebral depth, using the surgeon's finger approaching the contralateral vertebral body wall or by assessment of vertebral depth at the discectomy level adjacent to the vertebra to be instrumented. The screw platform is then inserted in the desired orientation and screwed into place using a screw driver with the main vertebral body screw. Then the second smaller anchor screw is secured to the vertebra. Finally, the rods are locked to the screw-head platform. If there are multiple rods of different sizes, the larger diameter rod is secured first and then the smaller diameter rod.

BRIEF DESCRIPTION OF THE DRAWINGS

The foregoing summary, as well as the following detailed description of illustrative embodiments of the device of the present application, will be better understood when read in conjunction with the appended drawings. For the purposes of illustrating the device of the present application, there is shown in the drawings illustrative embodiments. It should be understood, however, that the application is not limited to the precise arrangements and instrumentalities shown. In the drawings.

DETAILED DESCRIPTION OF THE DRAWINGS

Figure 1:
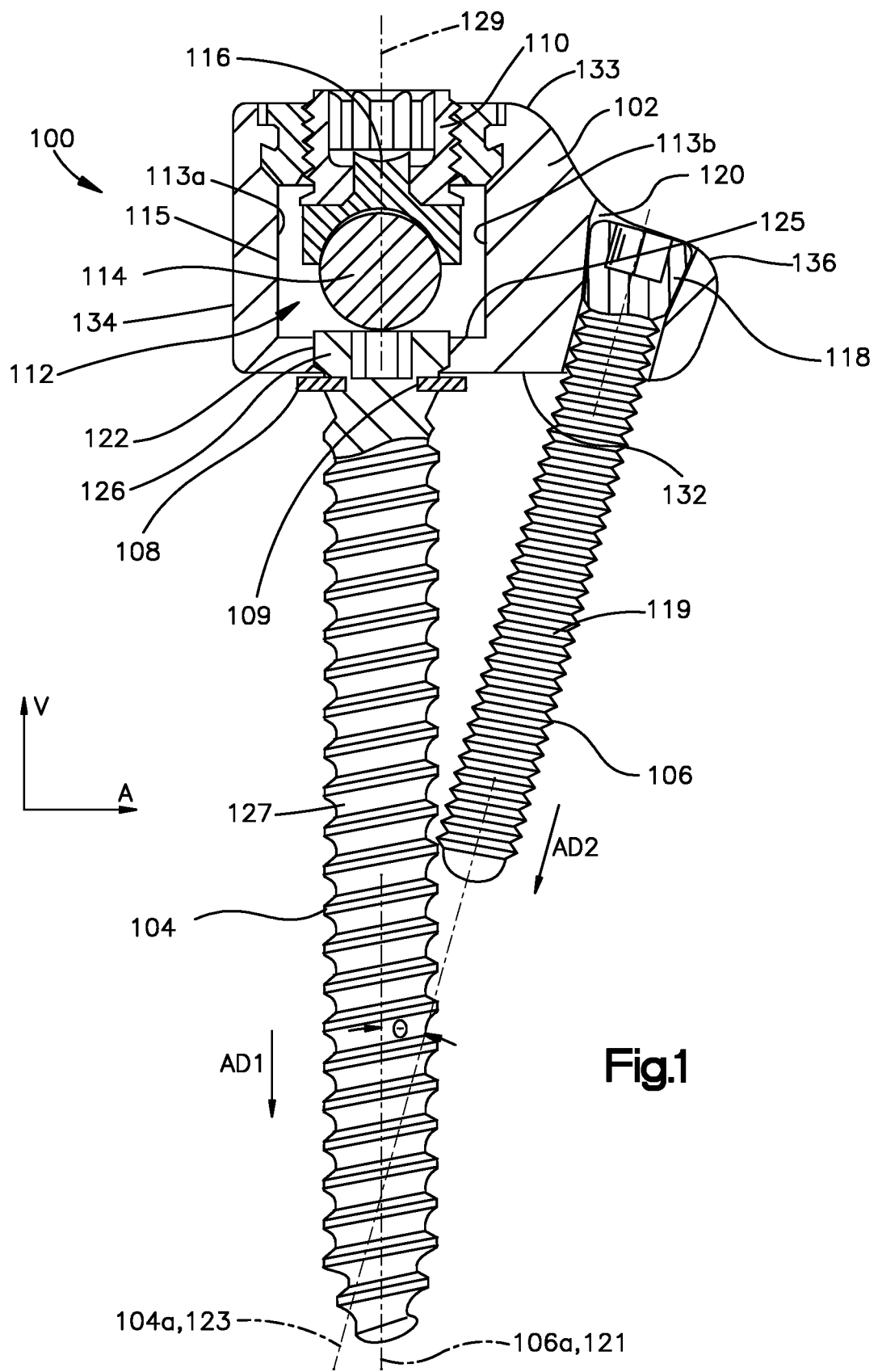
FIG. 1 is a cross-sectional view of a device for correcting a spinal deformity taken along lines 1-1 in FIG. 2, according to a first embodiment of the present disclosure.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Figure 2:
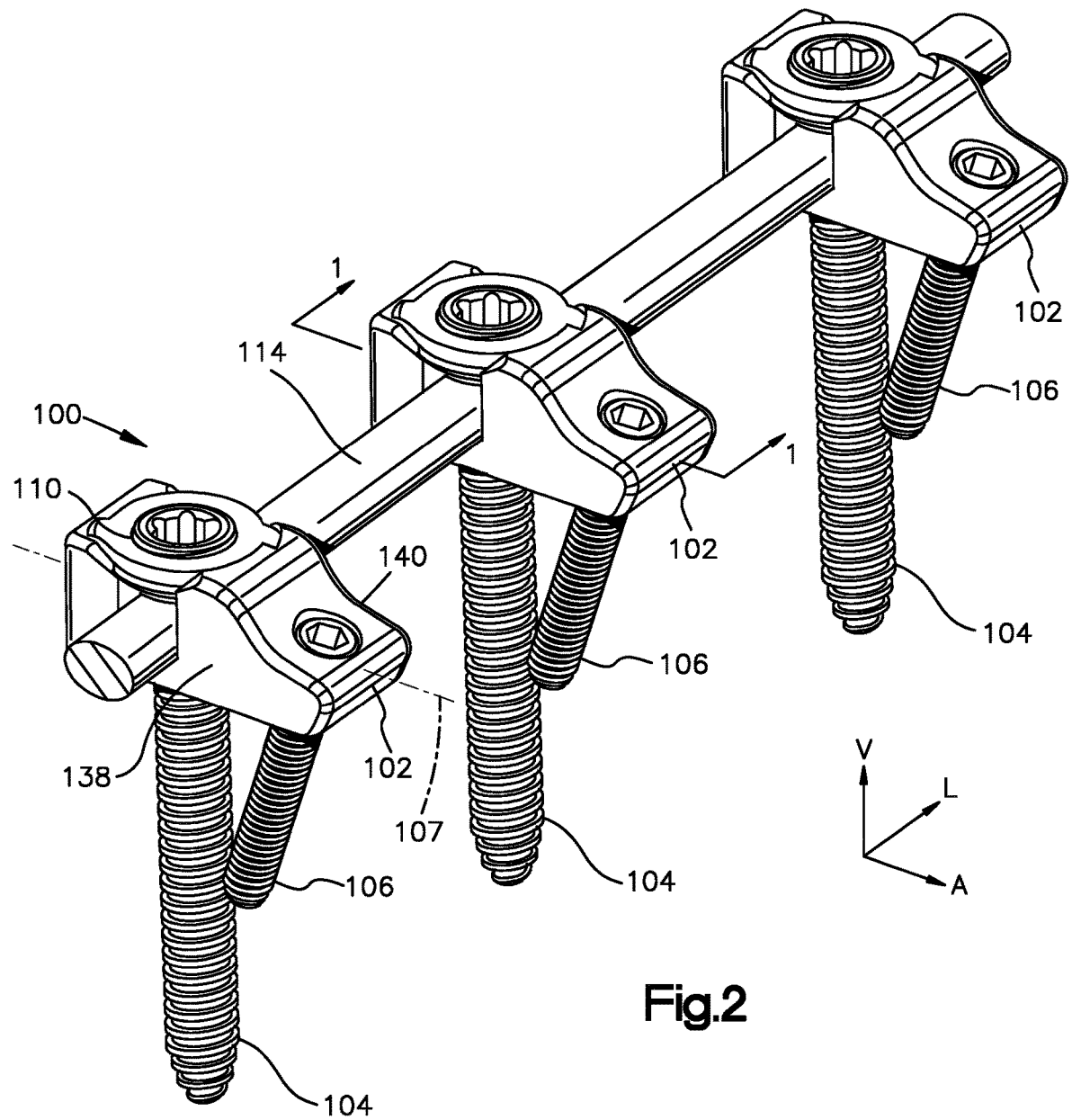
FIG. 2 is a perspective view of a device according to the first embodiment of the present disclosure.

Referring to FIGS. 1 and 2, the device 100 includes a platform member 102, referred to herein as a screw-head platform 102, a first anchor or main vertebral body screw 104, and an second anchor 106 or anchor screw 106. The platform member 102 can define one or more recesses configured to receive at least one elongate corrective rod 114. The main vertebral body screw 104 is rotatably connected to the platform member 102 while also being configured to secure to a vertebral body (not shown). The main vertebral body screw 104 can secure the platform member 102 to the vertebral body. In addition, the second anchor 106 can be inserted though the platform member 102 into the vertebral body. The platform member 102 is configured such that the anchor screw 106 is aligned at an oblique angle relative to the main vertebral body screw 104 and is disposed in common plane 107 with the main vertebral body screw 104, as further detailed below. The screw-head platform 102 can attach one or more corrective elongate rods, for instance a primary rod 114 (FIGS. 1-2) and a secondary rod 224 (FIGS. 3-6), to the patient's spine in order to correct the spinal deformity. Further, the screw-head platform 102 is configured to have a low-profile and low volume. A screw-head platform 102 with a low profile or distance relative to the vertebra and a low volume can accommodate the limited spaced constraints around the spine as noted above. Further, the main vertebral body screw 104 can be connected to the screw-head platform 102 a retention component 108. The retention component 108, which in the drawing is illustrated as a C-clip, protrudes into an indentation 109 defined by the main vertebral body screw 104. The retention component 108 resists movement of the main vertebral body screw 104 relative to the screw-head platform 102 along the vertical direction V as further detailed below. The device also includes a locking means, for instance a top-loading screw 110 or threaded plug 110 that can secure the primary rod 114 in the primary recess 112.

Referring to FIGS. 1 and 2, the first anchor 104 and the second anchor 106 can are configured to engage with the screw-head platform and the vertebral body. The first and second anchors 104 and 106 can be any device configured to anchor or secure to a bone. For instance, the first anchor 104 includes a head 126 and a shaft 127 that extends from the head 122 along a screw axis 104a. Further, the second anchor includes a head 118 and shaft 119 that extends from the head along a second screw axis 106a. The screw axes 104a and 106a can extend along, and are aligned with, the axial directions AD1 and AD2 of respective anchors. Further, the first and second anchors can be entirely threaded (FIGS. 3 and 5), or partially threaded (FIG. 1) along an outer surface thereof. The phrase "first anchor" is used interchangeably with the phrase "main vertebral body screw" and the phrase the "second anchor" is used interchangeably with the phrase "anchor screw" throughout the present disclosure.

Continuing with FIGS. 1 and 2, the platform 102 is configured to position the first anchor 104 relative to the second anchor 106, and also to attach one or more corrective rods to the vertebrae of a spine. The platform 102 defines upper surface 133 and a lower surface or underside 132 spaced from the upper surface 133 along the vertical direction V. The platform member 102 defines opposed sides 134 and 136 that are spaced apart along the lateral direction A, and opposed ends 138 and 140 (FIG. 2) spaced apart along the longitudinal direction L. The device 100 is described herein as extending along a longitudinal direction "L", a lateral direction "A", and vertically along a vertical or transverse direction "V". Unless otherwise specified herein, the terms "longitudinal," "lateral," and "vertical" are used to describe the orthogonal directional components of various device components and device component axes. It should be appreciated that while the longitudinal and lateral directions are illustrated as extending along a horizontal plane, and that the vertical direction is illustrated as extending along a vertical plane, the planes that encompass the various directions may differ during use. For instance, when the device is implanted, the longitudinal direction L extends generally along the caudal-cranial direction. The horizontal plane defined by the lateral direction A and vertical direction T lies generally in the anatomical plane defined by the anterior-posterior direction, and the medial-lateral direction.

Referring again to FIGS. 1 and 2, the platform 102 is configured such that the main vertebral body screw 104 is prevented from moving along the vertical direction V relative to the screw-head platform 102, which provides improved angular stability as discussed above. Further, a screw-head platform 102 that aligns a main vertebral body screw 104 in the same plane as an anchor screw 106, for instance along the lateral direction A, reduces the required size of the screw-head platform 102, in particular, in the longitudinal direction L (or the cranial-caudal direction) when implanted. The result is a more efficient use of space inside the vertebral body, in particular, thoracic and cervical vertebral bodies, to which the device will be affixed, where space is limited. Further, the triangulation of the screws increases the resistance against pull out and cyclic loads.

As can be seen in FIGS. 1 and 2, the screw-head platform 102 defines a primary recess 112 for receiving the primary elongate rod 114. The primary recess 112 can be in the form of a U-shaped channel running through the screw-head platform 102 along the longitudinal direction L. For instance, the platform 102 can define the recess wall 115 that extends from the upper surface 133 the vertical direction V toward underside 132. The recess 112 can have an open top or upper portion. The platform 102, and in particular the recess wall 115 includes first and second recess sidewalls 113a and 113b that are spaced apart from each other along the lateral direction L, and recess base 125 that is spaced from the upper surface 133. The U-shape recess 112 thus permits the primary rod 114 to be easily inserted into the recess 112. Further, the recess 112 has a width W that corresponds approximately to the diameter D of the primary rod 114. The width W can be the dimension that extends between the opposed first and second recess sidewalls 113*a* and 113*b*. When the width W is about the same as the diameter D of the primary rod 114, the rod 114 can be inserted into the recess 112 while reducing lateral movement, i.e. along the lateral direction L, of the rod within the recess 112. Decreased rod movement increases the overall mechanical stability of the device when implanted.

The shape of the recess 112 can assist in securing the rod 114 in place. For instance, shape of the primary recess 112 can be complementary to the shape of the primary rod 114. Increased contact area between the screw-head platform 102 and the primary rod 114 can also reduce the potential movement, particularly lateral movement along the lateral direction A of the primary rod 114 when the rod 114 is fully seated in the primary recess 112. The device 100 can an additional securing member, such a component 116 can that is configured to restrict movement, in particular lateral movement, of the primary rod 114 in the recess 112. The component 116 may be integral with or separate from the locking means described herein. Further, the primary recess as described herein is similar to the secondary recess configured to receive therein the secondary rod.

Referring to FIGS. 1 and 2, the underside 132 of the screw-head platform 102 is configured to face the vertebra when the device is implanted. In an embodiment, the underside 132 of the platform 102 is shaped in a complementary manner to the surface of the vertebra to which it is to be attached. In this way, the height of the screw-head platform 102 can be minimized, for instance the height of the platform 102 off the vertebra when implanted can be minimized. The underside 132 of the screw-head platform 102 can be concave. For instance, the underside can be concave with respect to a first axis (not shown) that is substantially perpendicular to the longitudinal L and vertical V directions. The first and second anchors 104 and 106 protrude through the underside 132 as to affix the screw-head platform 102 to the vertebra.

The screw-head platform 102 is generally elongate in shape along the lateral direction A. The elongate shape of the screw-head platform 102 accommodates the main vertebral body screw 104 and an anchor screw 106. For instance, the screw-head platform 102 defines a main or first bore 122 for receiving the main vertebral body screw 104, and an anchor bore or second bore 120 for receiving the anchor screw 106. The main bore 122 extends along a main bore axis 123. In the illustrated embodiment, the main bore 122 extends from the base 125 of recess to the underside 132 of the platform 102 along the vertical direction V such the main bore axis 123 and the vertical direction V are aligned. Further, the anchor bore 120 extends along and defines anchor bore axis 121, wherein the anchor bore axis 121 and the main bore axis 123 define an angle θ that extends therebetween. As noted above, the angle θ is oblique, and is preferably less than 90 degrees. The main bore 122 and the anchor bore 120 are configured to align the anchor screw 106 at an oblique angle relative to the main vertebral body screw 104 and in a common plane 107 with the main vertebral body screw 104 along the lateral direction A. For instance, the main bore axis 123 and the anchor bore axis 121 lie in a common plane 107 that extends along the lateral direction A. When the main vertebral body screw 104 is disposed in the main bore 122, the main vertebral body screw extends along the main bore axis 123, and when the anchor screw 106 is disposed in the anchor bore 120, the anchor screw 106 extends along the anchor bore axis 121. In such a configuration, the screw axes 104*a* and 106*b* are coaxial with the main bore axis 123 and the anchor screw axis, respectively.

The main bore 122 sized to receive the main vertebral body screw 104. The main bore 122 may be shaped to have a complementary surface to the underside 132 of the head 118 of the main vertebral body screw 104 so that the main vertebral body screw 104 is supported in its axial direction AD1 when the main vertebral body screw 104 is fully seated within the main bore 122. The main bore 122, and the head 118 of the main vertebral body screw 104, may be accessed through the recess 112. After insertion of the primary rod 114 in the primary recess 112, the primary rod 114 obstructs access to the main bore 122 or the head 118 of the main screw in the primary recess 112.

The main vertebral body screw 104 may be rotatably connected to the screw-head platform 102. This has the effect of restricting the axial movement of the main vertebral body screw 104 relative to the screw-head platform 102, while still allowing relative rotational movement the screw 104. As noted above, the screw-head platform 102 may comprise a retention component 108 to perform the function of connecting the screw-head platform 102 to the main vertebral body screw 104, restricting relative axial movement while allowing relative rotational movement. Such a retention component 108 may be an integral part of the screw-head platform 102 or it may be a separate component 116 that is attached to the screw-head platform 102. By restricting relative axial movement of the main vertebral body screw 104, but allowing relative rotational movement thereof, the main vertebral body screw 104 to be screwed into the vertebra body of the patient while maintaining the screw-head platform 102 in the desired rotational orientation. In order to provide the connection between the main vertebral body screw 104 and the screw-head platform 102, the main vertebral body screw 104 may have an annular indentation 109. The retention component 108 that can be disposed at least partially with this annular indentation 109 in order to constrain the axial movement of the main vertebral body screw 104. In particular, the retention component 108 can be carried by the underside 132 of the platform and adjacent to the main bore 122 to protrude into the annular indentation 109 provided on the main vertebral body screw 104 and so constrain its axial movement. It will be appreciated that a protrusion that closely fits within the annular indentation 109 can minimize the play between the retention component 108 and the annular indentation 109.

Continuing with FIGS. 1 and 2, the retention component 108 referred to above may be integral to the screw-head platform 102 or it may be a separate component 116 which is subsequently secured to the screw-head platform 102 so as to perform the task of retaining the main vertebral body screw 104 relative to the screw-head platform 102. The retention component 108 may protrudes into the annular indentation 109 of the main vertebral body screw 104 all the way around the screw. However, the retention component 108 may only protrude into part of the annular indentation 109. For example, the retention component 108 may protrude into the annular indentation 109 so that it protrudes into between 180° to 360° of the annular indentation 109. An exemplary retention component 108 is a C-clip. Further, the retention component 108 may only protrude into less than 180° of the annular indentation 109 of the main vertebral body screw 104, as well as less than 90° of the annular indentation 109 of the main vertebral body screw 104. The retention component 108 may comprise a single continuous protrusion that is received in the annular indentation 109 of the main vertebral body screw 104. In other embodiments, the retention component 108 may comprise a plurality of discrete protrusions that protrude into the annular indentation 109. A higher the volume of the retention component 108 that protrudes into the annular indentation 109 of the main vertebral body screw 104, the more stable the axial constraint of the screw 104. Decreasing the proportion of the annular indentation 109 that receives a protrusion of the retention component 108 can lower the frictional resistance provided by the retention component 108 and permit greater rotational movement of the main vertebral body screw 104. Other retention components are of course possible as the skilled person would understand. For example, the retention component 108 could comprise a pin arranged to engage with the annular indentation 109. In one example, a pin or a plurality of pins may be passed through the screw-head platform 102 into the annular indentation 109, the pins then being fixed in position. In another embodiment, the pin or pins may be biased to protrude from the screw-head platform 102. In such an embodiment, the pin, or pins, are displaceable against the bias. This allows the main vertebral body screw 104 to be inserted into the main bore 122 of the screw-head platform 102 by displacing the pin, or pins, out of their protruding arrangement. The pin can resiliently snap back to protrude into the annular indentation 109 to restrict further axial movement of the main vertebral body screw 104. Where the retention component 108 comprises a plurality of discrete protrusions that protrude into the annular indentation 109, the plurality of discrete protrusions are arranged symmetrically when protruding into the annular indentation 109 of the main vertebral body screw 104. This can reduce the presence of less stable directions of the main vertebral body screw 104. Further, the plurality of discrete protrusions number at least three to ensure a certain level of stability is provided by the retention component 108.

As discussed above, the screw-head platform 102 may further comprise an anchor bore 120. The anchor bore 120 is sized to receive an anchor screw 106. The anchor bore 120 configured such that when it receives the anchor screw 106 therein, the anchor screw 106 is aligned at an oblique angle relative to the main vertebral body screw 104 as noted above. In other words, the anchor bore 120 configured to align the anchor screw 106 such the anchor screw axis 106a (that extends along the length of the anchor screw 106 or AD2) is angled with respect to screw axis 104a of the main vertebral body screw 104 (the main vertebral body screw axial direction AD1). Thus, the axial direction AD2 of the anchor screw 106 is neither parallel nor at a right angle to the axial direction AD1 of the main vertebral body screw 104. The combination of the anchor screw 106 in addition to the main vertebral body screw 104 improves the pull out resistance of the device 100.

The anchor screw 106 may have angular stability relative to the screw-head platform 102, which increases the overall reliability and stability of the device. The anchor bore 120 can includes a thread is configured to engage with a thread on the head 118 of the anchor screw 106 as the anchor screw 106 is secured into the anchor bore 120. It should be appreciated that the anchor screw 106 is configured such that the movement of the anchor screw 106 along the anchor bore axis 121 is not prevented in the same manner that axial movement of the main vertebral body screw 104 is limited. In this way, the anchor screw 106 will not necessarily be present when securing the main vertebral body screw 104 into the patient's vertebra, which could result in the anchor screw 106 interfering with this operation.

The angle θ between the main body vertebral screw 104 and the anchor screw 106 when both screws are properly seated in the screw-head platform 102 is based on the anatomical situation. In particular, it has been found that an angle θ of between 15° to 30° is particularly acceptable. In an exemplary embodiment, angle θ can be approximately 20°. It should be appreciated that the angle θ can be defined as the angle between the screw axes 104a and 106a, the angle between the main bore axis 123 and the anchor bore axis 121, or the angle between the axial directions AD1 and AD2.

As discussed above, the platform 102 has compact size. The height of the screw-head platform 102 is approximately 15 mm or less, for example, the height of the screw-head platform 102 may be 12 mm or may be 10 mm. The height of the screw-head platform 102 is the distance measured perpendicular from the screw-head platform 102 surface that faces the vertebral body 434 in use to the surface opposite. In other words, the screw-head platform 102 height is a measure of how far the screw-head platform 102 rises above the underside 132 of the screw-head platform 102. Ensuring that the height of the screw-head platform 102 is as low as possible improves the space efficiency of the device and reduces the interference caused by the screw-head platform 102 in situ.

The screw-head platform 102 is of a generally rectangular shape. Specifically, the underside 132 of the screw-head platform 102, which contacts the vertebra body, is a rectangular shape so as to accommodate the screws and the rods. The length L (not shown) measured between opposed ends 138 and 140 of platform is no greater than 30 mm. Further, the length L of the platform is no greater than 25 mm. In addition, the width X (not shown) measured between opposed sides 134 and 136 of the screw-head platform 102 is no greater than 30 mm. Further, the width X (not shown) is no greater than 25 mm. or less. Such a size keeps the screw-head platform 102 compact.

As described above, the device 100 may comprise one or more elongate corrective rods or elongate members configured to be received in the primary recess 112 of the platform member 102. The primary rod 114 can have a diameter that is greater than 5.0 mm. Alternatively, or in addition, the primary rod 114 can have a diameter that is 5.5 mm or less. In an exemplary embodiment, the primary rod 114 can have a diameter of about 5.5 mm. Further, the primary rods 214, 314, and 414 of the second, third and fourth embodiments can have similar dimensions. In accordance with alternative embodiments, the device may also include a secondary rod 224, 324, 424 (FIGS. 3-6) configured to be received and secured in the secondary recess 226, 326, 426 Further, the secondary rod 224, 324, 424 can have a diameter of 4.0 mm or less.

The device as described herein may be made from any suitable biocompatible material. For instance, the platform, first and second anchors, and locking means can be formed of any biocompatible material. Exemplary materials are metallic materials. Suitable metallic materials include cobalt-chrome alloys, titanium, and stainless steel.

Referring to FIG. 2, the device can include a plurality of the screw-head platforms 102, main vertebral screws 104, and anchor screws 106. The primary rod 114 is depicted as secured within the plurality of screw-head platforms 102 in the manner in which it is secured when the device is implanted in the body. The screw-head platform 102 is generally elongate in shape in a direction perpendicular to the length of the primary rod 114, or the lateral direction A, when the rod 114 is secured to the screw-head platform 102. The common plane 107 in which the main vertebral body screw 104 and the anchor screw 106 lie is also perpendicular to the length of the primary rod 114 when secured in the screw-head platform 102. In other words, the common plane extends along the lateral direction A and is perpendicular to the longitudinal direction L. In general, when in use the screw-head platforms 102 are secured to the lateral circumference of the vertebra body and the underside 132 of the screw-head platform 102 rests on the surface of the vertebra. The screw-head platform 102 is shaped with a curvature that enables the underside 132 of the screw-head platform 102 to fit best to the vertebra body. Such curvature will minimise the gap between the underside 132 of the screw-head platform 102 and the body of the vertebra. This also reduces the profile of the screw-head platform 102 off of the vertebra body.

The device of the present disclosure may comprise a locking means 110, 210, 310 for securing the primary rod 114, 214,314 to the screw-head platform 102, 202, 302. Further, as shown in FIGS. 3-6, the device may also include a locking means 220, 320 for securing the secondary rod 224 to the screw-head platform 102.

The locking means for securing the primary rod or the means for securing the secondary rod may comprise a top loading screw. A top loading screw seals the rod into the recess into which the rod is placed. In other words, the rod is placed in the open recess and the top loading screw secures the rod by blocking the top of the recess so that an enclosed channel is formed in which the rod is held therein. The rod is inhibited from rotating or sliding within the channel by the top loading screw applying a sufficient pressure to the rod. A top loading screw as a securing means can be used for just one of the primary recess or secondary recess. Alternatively, a top loading screw can be used as a securing means with both the primary recess and the secondary recess.

For instance, referring to FIGS. 1 and 2, the locking means 110, which can include a top-loading screw or threaded plug 110, secures the primary rod 114 in the recess 112. The top loading screw 110 can be unscrewed and removed in order to open the U shaped the recess 112, which can allow the primary rod 114 to be removed or inserted into the primary recess 112. The top loading screw 110 defines a central screw axis 129. When the top loading screw 110 is secured to the rod 114, the central screw axis intersects a central rod axis of the rod 114. In addition, the top loading screw 110 can be rotatably connected to a rod holding component 116 shaped in a complementary manner to the primary rod 114 in order to aid in securing the primary rod 114 in the primary recess 112. Component 116 contacts approximately half the cross-sectional circumference of the primary rod 114 and transfers the restraining force of the threaded plug 110 to the primary rod 114. While a top-loading screw 110 is shown in FIG. 1 for secure the primary rod 114 in place, a side-loading screw can be used as well. The side loading screw is further detailed below. The use of a top loading screw is advantageous as it provides an easier way of securing a rod. This is due to the relatively wide tolerance in the position of the rod prior to the commencement of securing using the top loading screw. Screwing of the top loading screw then gradually confines the rod to its secure position within the recess. Top loading screws also reduce the length and/or width requirements of the screw-head platform as they secure the rod from above. Whereas, the use of side loading screws, further detailed below, can require additional room within the screw-head platform in which to accommodate a screw.

Figure 3:
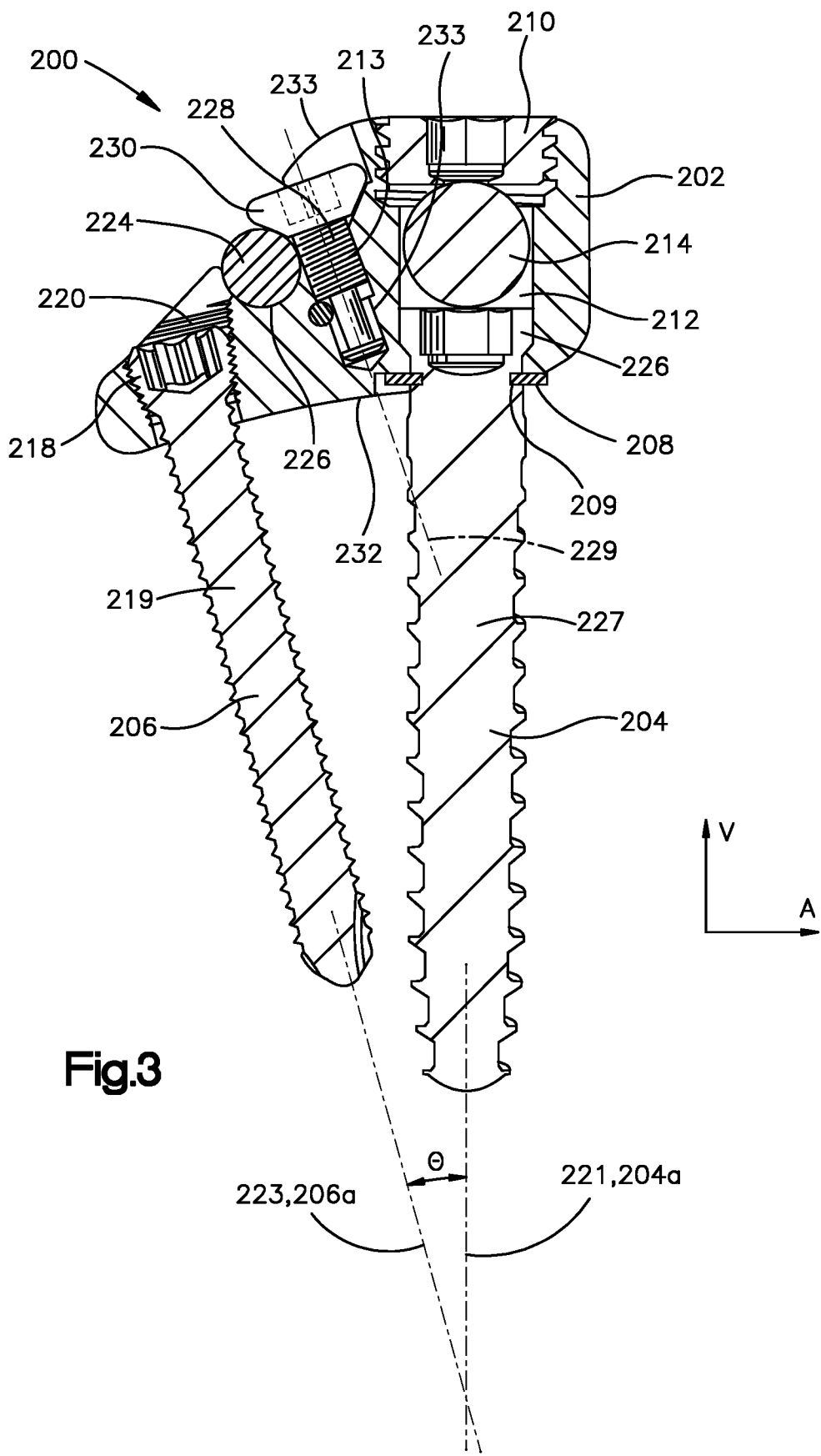
FIG. 3 is a cross-sectional view of the device illustrated in FIG. 4, taken along line 3-3 thereof, according to a second embodiment of the present disclosure.
Figure 4:
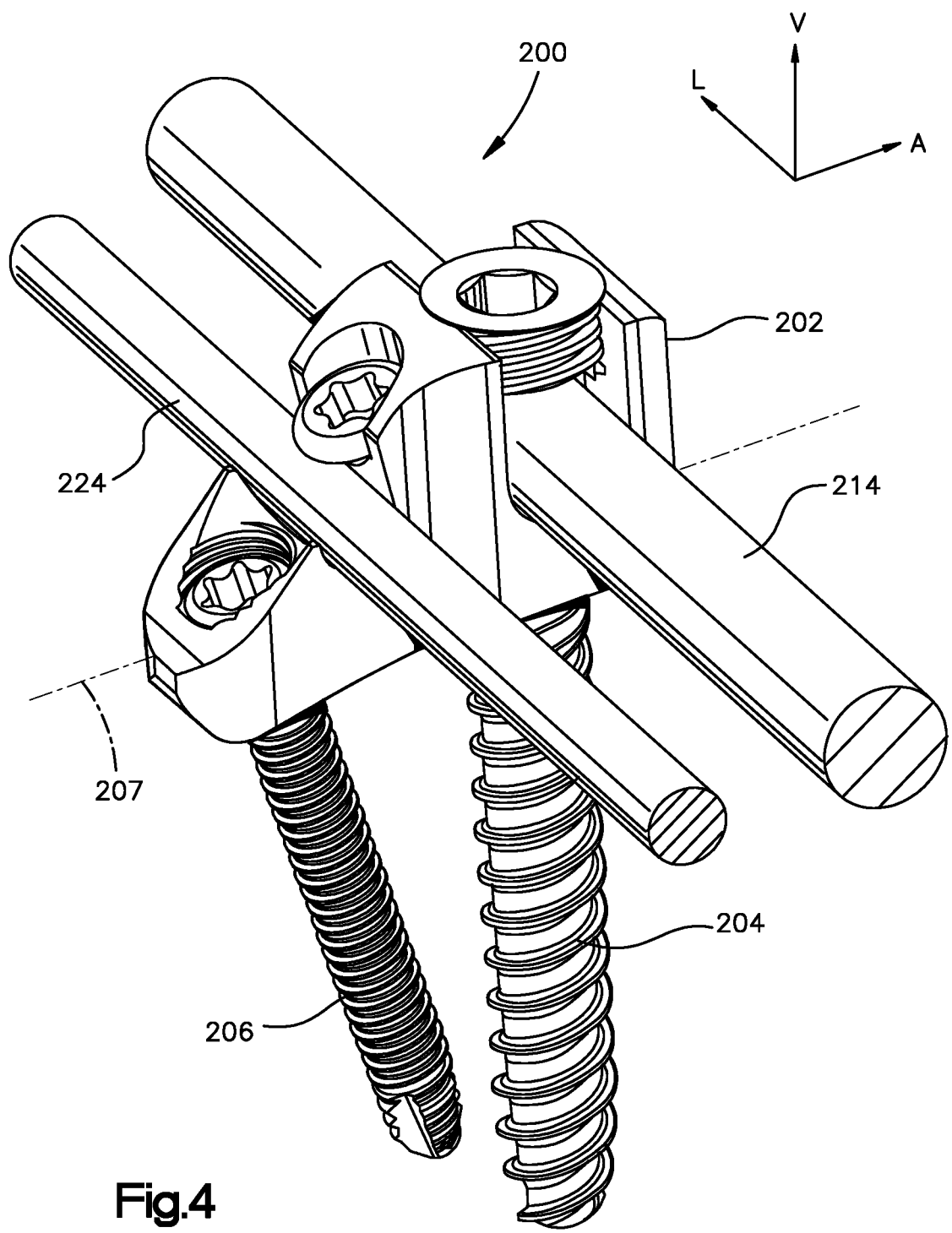
FIG. 4 is a perspective view of a device shown in FIG. 3, according to the second embodiment of the present disclosure.

Referring now to FIGS. 3 and 4, the device 200 illustrated in FIGS. 3 and 4 have similar components to the device illustrated in FIGS. 1 and 2 and described above. Accordingly, features and aspects of the first embodiment are interchangeable with the features and aspects of the second embodiment. In accordance with the alternative embodiment, the device includes a secondary recess for receiving a secondary spinal rod 224. For instance, the device 200 includes a screw-head platform 202, a first anchor 204 or main vertebral body screw 204 and a second anchor 206 or an anchor screw 206, as well as a primary rod 214 in the primary recess 212 of the screw-head platform 202. The main vertebral body screw 204 is connected to the screw-head platform 202 via the retention component 208. Further the platform 202 includes a main or first anchor bore and second bore or anchor bore that is configured similarly to the main and anchor bore described above with respect to FIGS. 1 and 2. In accordance with the embodiment illustrated in FIGS. 3 and 4, the anchor screw 206 includes a head 218 and shaft 219 that extends from the head 218 along an anchor axis 206b. The head 218 of the anchor screw 206 includes a threaded outer surface that corresponds to threads on the inside of the anchor bore 220 of the platform 202. The threaded anchor screw 206 aids in angular stability of the anchor screw 206 with respect to the screw-head platform 202. The primary rod 214 is secured in the primary recess 212 by the presence of a top loading screw 210, similar to the top loading screw 110 described above. The platform 202 also defines a cavity, which defines the primary recess 212 for receiving the primary rod 214. The cavity extends partially between the main vertebral body screw 204 and the top loading screw 210 within which the primary rod 214 can be secured. The width of the cavity corresponds approximately to the diameter of the primary rod 214.

Referring to FIG. 3 the screw-head platform 202 is shaped to receive a primary rod 214. The screw-head platform 202 includes a secondary recess 226, similar to the primary recess 212, for receiving a secondary rod 224. The secondary recess 226 runs parallel to the primary recess 212 in order to receive a secondary rod 224 that is parallel to a primary rod 214. The secondary recess 226 is sized in accordance with the size of the secondary rod 224 that is to be used. The secondary recess 226 is a semi-circular channel that contacts the secondary rod 224 around approximately half of the cross-sectional circumference of the secondary rod 224. The secondary rod 224 is secured in the secondary recess 226 by the use of a side loading screw 210. The main vertebral body screw 204 is connected to the screw-head platform 202 in a similar manner to that shown with the device of FIG. 1. Also, the anchor screw 206 and the main vertebral body screw 204 are at an oblique angle to each other and within a common plane as noted above, similar to the embodiment shown in FIGS. 1 and 2. Accordingly, the common plane is perpendicular to the longitudinal direction L of the platform 202 and length of the primary rod 214 and the secondary rod 224. The underside 232 of the screw-head platform 202 is shaped in a complementary manner to the vertebra surface to which it will be attached.

In accordance with an alternative embodiment, the present disclosure includes a side loading screw 228, 328 for securing the primary rod 214 or for securing the secondary rod 224 in respective recesses. As can be seen n FIGS. 3 and 4, an embodiment of a side loading screw 228 is shown positioned adjacent the second recess 226 and at least partially in a screw bore 233. The side loading screw 228 includes a conical head 230 and shaft 213 that extends from the head 230 along central screw axis 229. The side loading screw 210 is attached to the platform 202 such that the central screw axis 229 is offset, or does not intersect, a central elongate axis of the second rod 214. The shaft 213 is disposed in the bore 233 and the conical head 230 overhangs at least a portion of the recess 226 when the side-loading screw 228 is attached to the platform 202. The head 230 of the side loading screw 228 at least partially defines the secondary recess 226 or channel through which the secondary rod 224 runs. Tightening the side loading screw can decrease the gap between the head 230 and recess 226 and loosening the side loading screw 228 increases the gap into which the rod 214 can be placed. In other words, unscrewing the side loading screw 228 increases the space into which the secondary rod 224 can be placed and subsequently secured by tightening the side loading screw 228 so that the conical head 230 contacts and secures the secondary rod 224. After placing of the rod 214 in the recess 212 beneath the conical head 230 of the side loading screw 228, the screw 228 is tightened so that the rod 214 is held in position by the conical head 230. Such a side loading screw 228 does not increase the overall height of the device for a given mechanical stability when compared to top loading screws 110 and/or 210.

Although any combination of top loading and side loading screws can be used with the device of the present disclosure, it is has been shown that a top loading screw is easier to use with regard to the securing of the first rod into the screw-head platform 202. The secondary rod 224 can be secured by either a side loading screw 228 or a top loading screw 210 which will result in the relevant advantages described above. It is possible to use a side loading screw 228 for securing both the primary rod 214 and the secondary rod 224. However, the use of two side loading screws would make the platform longer, which could be problematic in certain spinal deformity surgery such as with adolescent vertebrae, where space within the patient is restricted. In particular, it is possible have a top loading screw 210 for securing the primary rod 214 and a top loading screw 210 for securing the secondary rod 224. Alternatively, it is possible to have a top loading screw 210 for securing the primary rod 214 and a side loading screw 228 for securing the secondary rod 224 as illustrated.

FIG. 4 depicts the device of FIG. 3 in a perspective view with a primary rod 214 and secondary rod 224 secured to the screw-head platform 202 in a manner similar to that in which the device is used within the body for supporting and manipulating a spinal deformity.

Figure 5:
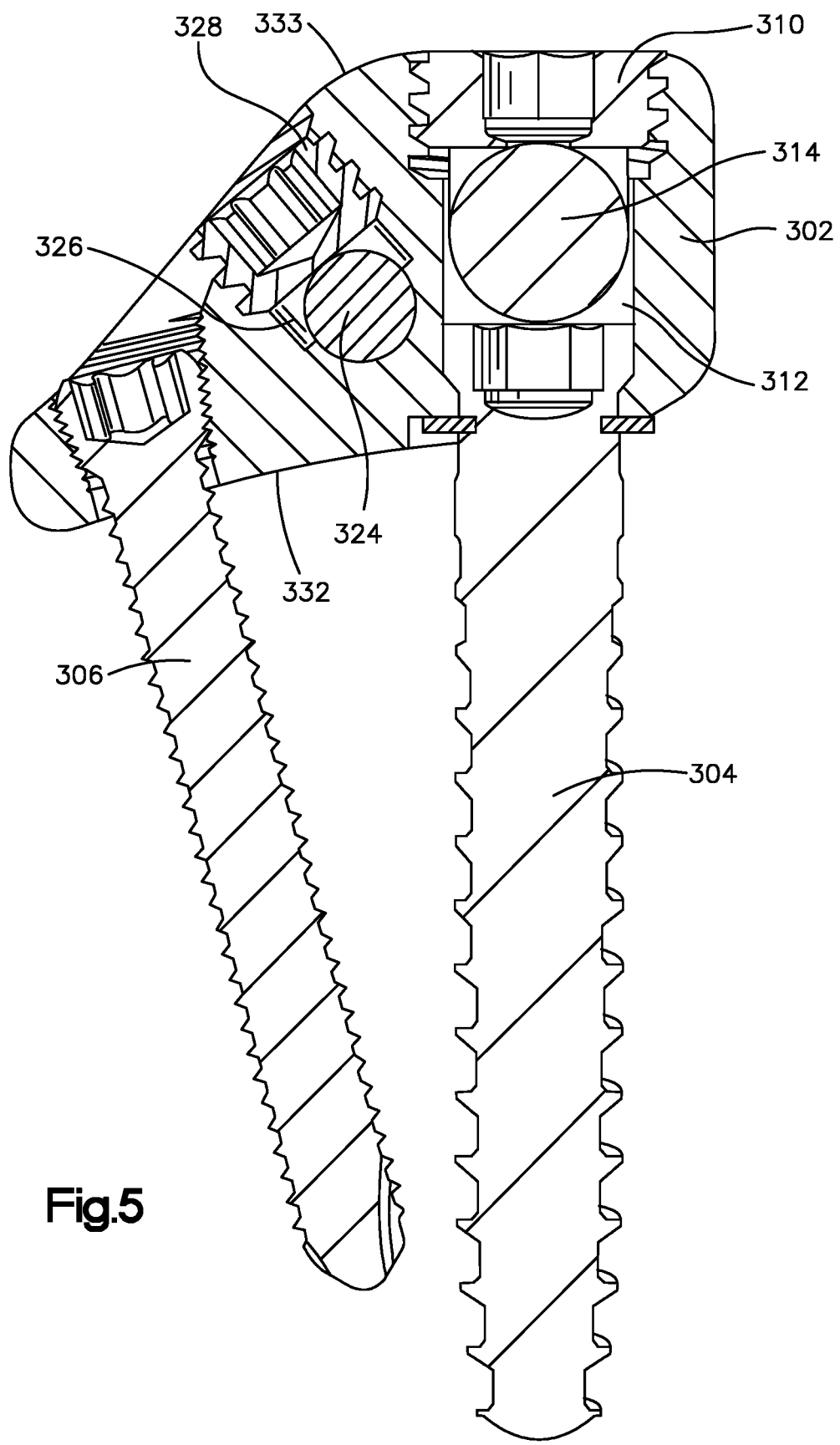
FIG. 5 is a sectional view of a device according to a third embodiment of the device of the present disclosure.

FIG. 5 illustrates a device 300 similar to the device 100 and 200 as described above. In accordance with the alternate embodiment shown in FIG. 5, the device 200 includes a top loading screw 328 for securing the secondary rod 324 to the screw-head platform 302. The screw-head platform 302 is shaped to receive a primary rod 314. The screw-head platform 302 may also comprise a secondary recess 326, similar to the primary recess 312, for receiving a secondary rod 324. The secondary recess 326 runs parallel to the primary recess 312 in order to receive a secondary rod 324 that is parallel to a primary rod 314. The secondary recess 326 is sized in accordance with the size of the secondary rod 324 that is to be used. The secondary recess 326 has a semi-circular channel at its base, which receives and supports the secondary rod 324 by contacting the secondary rod 324 around approximately half of its cross-sectional circumference. The top loading screw 328 contacts the secondary rod 324 to retain it in the semi-circular channel of the secondary recess 326.

Figure 6:
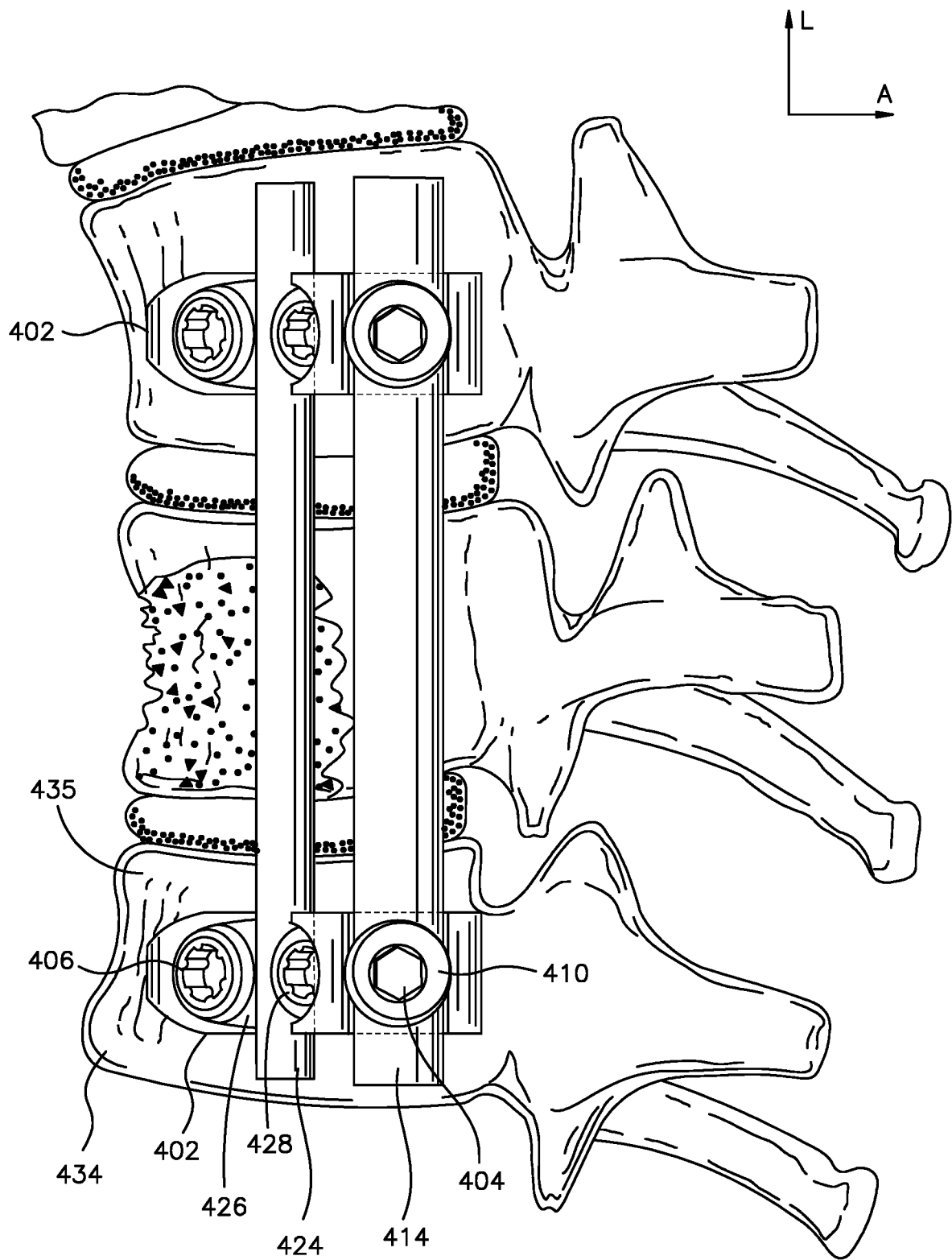
FIG. 6 illustrates a device according to third embodiment of present disclosure shown implanted in situ in the patient's body.

FIG. 6 depicts a device of the present disclosure in place within the patient's body. It can be seen that the screw-head platforms 402 are fixed to the vertebral body 434 and the primary rod 414 and secondary rod 424 are secured to the screw-head platform 402 so as to offer support to the spine and help counteract the spinal deformity. As described above, the device of the present disclosure is implanted by first exposing a lateral surface 435 of the vertebral body 434. The first screw-head platform 402 is then affixed to a designated vertebra by initially drilling a pilot hole and then screwing the main vertebral body screw 404 into the pilot hole, through the screw-head platform 402, and into the vertebral body 434. On fully tightening the main vertebral body screw 404, the screw-head platform 402 is positioned to extend from the posterior to the anterior of the vertebra and is held in position by the main vertebral body screw 404. Next, the anchor screw 406 is screwed into the vertebral body 434 to secure the screw-head platform 402. Next, further screw-head platforms 402 are affixed to other vertebra in a similar manner as described for the first screw-head platform 402. The primary rod 414 is then secured into the screw-head platforms 402, one at a time, by placing the primary rod 414 into the primary recess 412 of the screw-head platform 402 and securing it in place by applying and tightening a top loading screw 410. The securing of the primary rod 414 into each of the screw-head platforms 402 may require the manipulation of the spine. It is this manipulation that the device of the present disclosure supports. Next, the secondary rod 424 is secured into the screw-head platforms 402, one at a time, by placing the secondary rod 424 into the secondary recess 426 and tightening a side loading screw 428. This further supports the manipulated spine. The method has been described with reference to a particular embodiment of the present disclosure but it should be clear that the general features of the method can be utilised with any devices of the present disclosure.

Each of the plurality of screw-head platforms 102, 202, 302, 402 can have the features described above. In particular, each of the screw-head platforms 102 may comprise the same features or different features to each of the other screw-head platforms 102. In particular, each of the plurality of screw-head platforms 102 have a main vertebral body screw 104 associated with therewith so that each platform can be secured to the patient's spine, offering support and allowing manipulation.

The present disclosure also provides a kit for the correction of spinal deformity. The kit includes a screw-head platform 102, wherein the screw-head platform 102 comprises a primary recess 112 for receiving a primary rod 114 and a main bore 122 for receiving a main vertebral body screw 104; a main vertebral body screw 104; and a retention component 108 for connecting the screw-head platform 102 to the main vertebral body screw 104 so that the main vertebral body screw 104 cannot move relative to the screw-head platform 102 in the axial direction of the main vertebral body screw 104. Such a kit of parts may comprise additional features or parts as recited above. The kit of parts for assembling a device of the present disclosure enables the device to be in a disassembled state for ease of transport and to be then subsequently assembled before or during the operation in which it will be used.

The present disclosure also provides a method of correcting a spinal deformity using an anterior approach with the devices of the present disclosure. The method includes the step of affixing a screw-head platform to a patient's spine by screwing the main vertebral body screw into the lateral surface of the vertebral body and inserting the primary rod into the screw-head platform's primary recess. The method includes securing the primary rod within the primary recess. In addition, the method can include the step of affixing the anchor screw into the lateral surface of the vertebral body through the screw-head platform so as to further secure the screw-head platform in position. The anchor screw can be screwed into the vertebral body after the main vertebral body screw has been screwed into position. After inserting the primary rod into the primary recess, the primary rod may be secured within the primary recess by applying and screwing a top loading screw to contain the primary rod between the top loading screw and the screw-head platform. The method may also include affixing a plurality of screw-head platforms to the patient's spine and then inserting a primary rod into each of the screw-head platforms and securing the primary rod in each of these screw-head platforms. The insertion of the primary rod into each of the screw-head platforms may be associated with a level of spinal manipulation. The securing of the primary rod then holds this manipulation in place. The patient's spine can be thus be manipulated and supported to correct the spinal deformity. The method may also comprise inserting a secondary rod into a secondary recess in the screw-head platform. This is then followed by the securing of the secondary rod within the secondary recess, either by applying and screwing a top loading screw or by screwing a side loading screw so as to contain the secondary rod between the screw-head platform and the screw. Securing of the secondary rod occurs after the securing of the primary rod, the primary rod being typically designed to withstand greater forces than the secondary rod. When there are a plurality of screw-head platforms present, the primary rod can be secured in all of the plurality of screw-head platforms before the secondary rod is secured in any of them. Alternatively, the primary rod and then the secondary rod can be secured into each screw-head platform, primary rod first, before commencing the insertion and securing of the primary rod and secondary rod in the next screw-head platform.

The device of the present disclosure can be implanted by performing a thoracotomy, a thoracolumbophrenotomy, or by using an endoscopic approach. For instance, the vertebral column is exposed and the lateral surface of the vertebral body is dissected to remove the soft tissue. A small awl is used to form a pilot hole for the main vertebral body screw. This pilot hole is usually close to the plane of the rib heads, parallel to the end plates in the axial plane, albeit perpendicular to the lateral vertebral body surface slightly directing anteriorly off the spinal canal. The length of the screw and screw tract preparation can be assessed based on previous MRI and/or CT based measurements of vertebral depth, using the surgeon's finger approaching the contralateral vertebral body wall or by assessment of vertebral depth at the discectomy level adjacent to the vertebra to be instrumented. The screw platform is then inserted in the desired orientation and screwed into place using a screw driver with the main vertebral body screw. Then the second smaller anchor screw is secured to the vertebra. Finally, the rods are locked to the screw-head platform. If there are multiple rods of different sizes, the larger diameter rod is secured first and then the smaller diameter rod.

It will of course be understood that the present disclosure has been described above purely by way of example, and that modifications of detail can be made within the scope of the invention.

What is claimed:
1. A spinal implant device comprising
 a first surface and a second surface that is opposite the first surface along a transverse direction, wherein the second surface is a bone facing surface,
 a first side and a second side that are opposite from one another along a longitudinal direction, perpendicular to the transverse direction;
 a first end, and a second end that is opposite the first end along a lateral direction, perpendicular to the transverse direction and the longitudinal direction, the spinal implant device defining:
 wherein the spinal implant device defines a main bore that extends along a central main bore axis that extends along the transverse direction, the main bore configured to receive a main vertebral body fixation element therethrough such that the main vertebral body fixation element is configured to extend into an underlying vertebra,
 wherein the spinal implant device defines an anchor bore that is offset from the main bore along the lateral direction and that extends along a central anchor bore axis, the anchor bore configured to receive an anchor fixation element therethrough,
 wherein the anchor bore does not pass through any rod receiving recesses, and
 wherein the first surface includes a convex portion that extends from the main bore and a concave portion that extends from the convex portion toward the second end.

2. The spinal implant device of claim 1, wherein at least a portion of the main bore is configured to receive a locking screw that secures a rod in a primary recess, the portion of the main bore having an upper surface and a lower surface,
 wherein the upper surface of the anchor bore is disposed below the lower surface of the portion of the main bore.

3. The spinal implant device of claim 1, wherein the spinal implant device has a first portion at the first end that defines a first height, and a second portion at the second end that defines a second height less than the first height.

4. The spinal implant device of claim 3, wherein the first height is measured from the second surface to the first surface, and the second height is measured from the second surface to the first surface.

5. The spinal implant device of claim 4, wherein the first surface at the second portion is offset from the first surface at the first portion with respect to the transverse direction.

6. The spinal implant device of claim 4, wherein the second surface at the second portion is substantially aligned with the second surface at the first portion with respect to the transverse direction.

7. The spinal implant device of claim 3, wherein the first height is from a select plane to the first surface, and the second height from the select plane to the first surface, wherein the select plane is defined at the second surface and is perpendicular to the central main bore axis.

8. The spinal implant device of claim 3, wherein the main bore extends into the first portion and the anchor bore extends into the second portion.

9. The spinal implant device of claim 1, wherein a line that intersects the central main bore axis of the main anchor bore and the anchor bore axis of the anchor does not intersect any other screw holes.

10. The spinal implant device of claim 1, wherein the spinal implant device is devoid of any screw holes between the main bore and anchor bore.

11. The spinal implant device of claim 1, wherein the spinal implant device is devoid of screw holes between the main bore and the first side and between the anchor bore and the second side.

12. The spinal implant device of claim 1, wherein the anchor fixation element is a screw and the anchor bore is threaded to receive a thread on a head of the screw.

13. A system comprising the spinal implant device of claim 1 and the main vertebral body fixation element that is configured to be inserted through the main bore and into the underlying vertebra.

14. A system comprising the spinal implant device of claim 1 and the anchor fixation element, wherein the anchor fixation element is an anchor screw that is configured to be inserted through the anchor bore and into the underlying vertebra.

15. The system of claim 14, wherein the anchor bore has internal threading, and the anchor screw has a head that is threaded to engage the threading of the anchor bore.

16. The spinal implant device of claim 1, wherein the concave and convex portions of the first surface are between the main bore and the anchor bore.

17. The spinal implant device of claim 1, wherein the convex portion is a first convex portion and the first surface includes a second convex portion between the concave portion and the second end.

18. The spinal implant device of claim 17, wherein the main bore includes a main bore perimeter at the first surface and the anchor bore includes an anchor bore perimeter at the first surface, and wherein the entire anchor bore perimeter is offset below the main bore perimeter with respect to the transverse direction.

19. The spinal implant device of claim 1, further comprising a screw-head platform that includes a primary recess configured to receive a primary rod.

* * * * *